United States Patent
Nose et al.

(10) Patent No.: US 7,577,236 B2
(45) Date of Patent: Aug. 18, 2009

(54) DEVICE FOR SWITCHING/GENERATING X-RAYS FOR DIAGNOSIS AND CURING

(75) Inventors: Hiroyuki Nose, Tokyo (JP); Daisuke Ishida, Tokyo (JP); Namio Kaneko, Tokyo (JP); Hisaharu Sakae, Tokyo (JP); Mitsuru Uesaka, Tokyo (JP); Atsushi Fukasawa, Tokyo (JP); Katsuhiro Dobashi, Chiba (JP)

(73) Assignees: IHI Corporation, Tokyo (JP); The University of Tokyo, Tokyo (JP); National Institute of Radiological Sciences, Chiba (JP)

( * ) Notice: Subject to any disclaimer, the term of this patent is extended or adjusted under 35 U.S.C. 154(b) by 91 days.

(21) Appl. No.: 11/913,970

(22) PCT Filed: May 11, 2006

(86) PCT No.: PCT/JP2006/309502

§ 371 (c)(1),
(2), (4) Date: Nov. 9, 2007

(87) PCT Pub. No.: WO2006/121125

PCT Pub. Date: Nov. 16, 2006

(65) Prior Publication Data

US 2009/0052625 A1 Feb. 26, 2009

(30) Foreign Application Priority Data

May 12, 2005 (JP) .............................. 2005-139720

(51) Int. Cl.
*G21G 4/00* (2006.01)
(52) U.S. Cl. ........................... 378/119; 378/62; 378/65; 378/116
(58) Field of Classification Search ................... 378/62, 378/64, 65, 91, 114–116, 119, 125
See application file for complete search history.

(56) References Cited

U.S. PATENT DOCUMENTS 6,332,017 B1   12/2001   Carroll et al.

FOREIGN PATENT DOCUMENTS

| JP | 08-096986 | 4/1996 |
| JP | 08-206103 | 8/1996 |
| JP | 09-129369 | 5/1997 |
| JP | 11-264899 | 9/1999 |

(Continued)

OTHER PUBLICATIONS

Dohashi, Katsunori, et al., "Development of Small-Sized Hard X-Ray Source using X-band Liniac," 2002. (in Japanese).

(Continued)

*Primary Examiner*—Jurie Yun
(74) *Attorney, Agent, or Firm*—Griffin & Szipl, P.C.

(57) ABSTRACT

There is disclosed a device including: an electron beam generation device 10 which accelerates a pulse electron beam 1 to transmit the beam through a predetermined rectilinear orbit 2; a laser generation device 20 which generates a pulse laser light 3; a laser light introduction device 30 which introduces the pulse laser light 3 onto the rectilinear orbit 2 so as to collide with the pulse electron beam 1; a metal target 42 which generates a particular X-ray 5 by collision with the pulse electron beam 1: and a target moving device 40 capable of moving the metal target between a collision position 2*a* on the rectilinear orbit and a retreat position out of the orbit.

5 Claims, 5 Drawing Sheets

FOREIGN PATENT DOCUMENTS

| | | |
|---|---|---|
| JP | 2001-133600 | 5/2001 |
| JP | 2001-176694 | 6/2001 |
| JP | 2002-280200 | 9/2002 |
| JP | 2003-038475 | 2/2003 |
| JP | 2003-151800 | 5/2003 |

OTHER PUBLICATIONS

Sasaki, M., et al., "Development of Mixed Dual-Energy X-Ray CT System," Medical Physics vol. 23, Supplement No. 2, Apr. 2003, pp. 158-161.

International Search Report issued in corresponding application No. PCT/JP2006/309502, completed Aug. 2, 2006 and mailed Aug. 8, 2006.

Fig.1

Prior Art

Fig.2

Prior Art

Fig.3

Prior Art

Fig.4

Prior Art

DEVICE FOR SWITCHING/GENERATING X-RAYS FOR DIAGNOSIS AND CURING

This is a National Phase Application in the United States of International Patent Application No. PCT/JP2006/309502 filed May 11, 2006, which claims priority on Japanese Patent Application No. 139720/2005, filed May 12, 2005. The entire disclosures of the above patent applications are hereby incorporated by reference.

BACKGROUND OF THE INVENTION

1. Field of the Invention

The present invention relates to an X-ray switching and generating device which switches and generates X-rays for diagnosis and curing.

2. Description of the Related Art

X-rays are electromagnetic waves having a wavelength of about 0.1 to 100 A ($10^{-11}$ to $10^{-8}$ m). Among the ray, an X-ray having a short wavelength (10 to 100 keV, $\lambda$=1 to 0.1 A) is referred to as a hard X-ray, and an X-ray having a long wavelength (0.1 to 10 keV, $\lambda$=100 to 1 A) is referred to as a soft X-ray. Moreover, an X-ray emitted at a time when an electron beam or the like is struck on a substance and having a wavelength inherent in a constituting element of the substance is referred to as a particular X-ray.

As apparatuses in which the X-rays are used, an X-ray transmission apparatus, an X-ray CT apparatus, an X-ray diffraction apparatus, an X-ray spectral apparatus and the like are utilized in broad fields such as a medical treatment, bioscience and material science. For example, to cure cardiac infarction, coronary angiography (IVCAG) in which an X-ray of about 50 keV is used is generally performed. Moreover, the X-ray CT apparatus is an apparatus in which an object to be measured is irradiated with X-rays from different directions to measure absorption of the rays, and an image is reconstructed by a computer to obtain a two-dimensional sectional image of the object.

As generation sources of the X-rays, an X-ray tube and synchrotron radiation light are known.

The X-ray tube is a device in which a thermion obtained by heating a filament in vacuum is accelerated at a high voltage, and is allowed to collide with a metal anode (target), thereby generating the X-ray. Examples of the X-ray to be generated from the X-ray tube include a continuous X-ray obtained by braking radiation of an electron, and a particular X-ray which is a bright line spectrum. The continuous X-ray is used as a light source for an application in which any X-ray having a specific wavelength is not required, for example, a transmission process for a medical treatment or industry. The particular X-ray is used for an application in which the X-ray having the specific wavelength is required, for example, X-ray diffraction, fluorescent X-ray spectroscopy or the like.

On the other hand, the synchrotron radiation light (SR light) is an X-ray generated during an orbit change in a case where an orbit of the electron beam accelerated at a speed close to a light speed is changed by a strong magnet in an annular accelerator (a synchrotron). The SR light is an X-ray source (e.g., an X-ray intensity (a photon number): about $10^{14}$ photons/s, a pulse width: about 100 ps) which is incommensurably intense as compared with the X-ray tube, and the light is used for a field in which a high X-ray intensity is required.

However, a synchrotron radiation light facility in which a synchrotron is used is a large-sized facility in which the synchrotron has a large diameter of about 50 m or more, and an orbit length reaches 100 m or more. Therefore, there is a problem that the facility even for a research or the medical treatment cannot easily be introduced. To solve the problem, a small-sized X-ray generation device is proposed in which a small-sized linear accelerator is used (e.g., Non-Patent Document 1).

On the other hand, in a conventional X-ray CT apparatus, a monochromatic meter including two crystal plates is used as means for obtaining a monochromatic hard X-ray from the radiation light. Since the monochromatic X-ray CT apparatus has a low measurement precision of an electron density, a mixed two-color X-ray CT apparatus is proposed in which two types of X-rays having different mixture ratios of a dominant wave and a higher harmonic wave are used (e.g., Non-Patent Document 2).

Moreover, Patent Document 1 has already been disclosed as a diagnosis and curing apparatus in which the particular X-ray is used as the X-ray for irradiation, and Patent Document 2 has already been disclosed as a diagnosis and curing apparatus in which the electron beam is used for curing and the X-ray is used for diagnosis.

Figure 1:
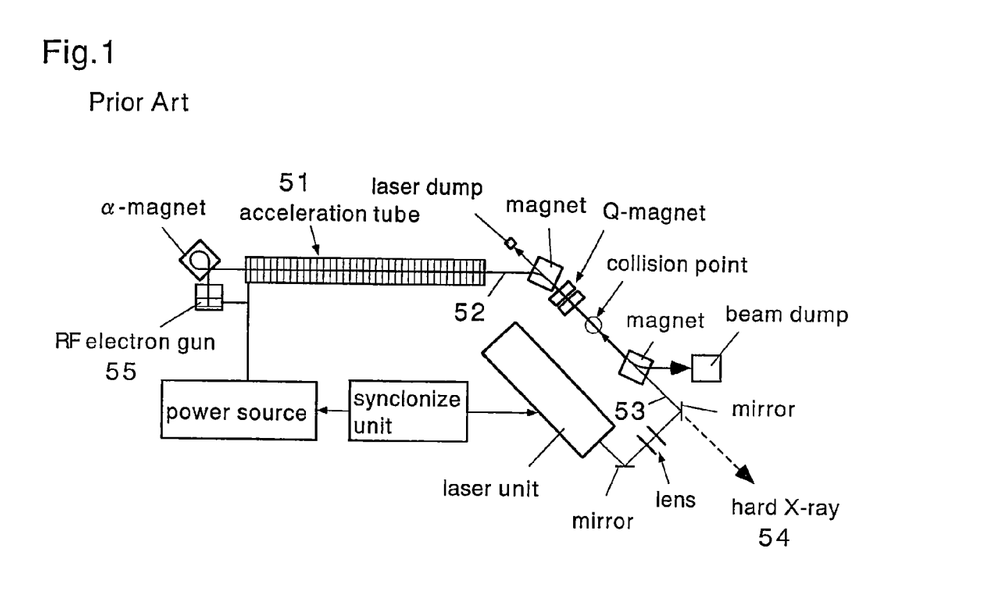
FIG. 1 is a schematic diagram of "Small-Sized X-Ray Generation Device" of Non-Patent Document 1.

In "Small-Sized X-Ray Generation Device" of Non-Patent Document 1, as shown in FIG. 1, an electron beam 52 accelerated by a small-sized accelerator 51 (an X-band acceleration tube) is allowed to collide with laser 53 to generate an X-ray 54. The multi-bunch electron beam 52 generated by an RF electron gun 55 (a thermal RF gun) is accelerated by the X-band acceleration tube 51, and collides with the pulse laser light 53. The hard X-ray 54 having a time width of 10 ns is generated by Compton scattering.

This device is miniaturized by using an X-band (11.424 GHz) corresponding to a frequency four times as high as that of an S-band (2.856 GHz) for general use in a linear accelerator as an RF for acceleration of the electron beam. For example, it is predicted that the hard X-ray having an X-ray intensity (the photon number) of about $1 \times 10^9$ photons/s and a pulse width of about 10 ps is generated.

Figure 2:
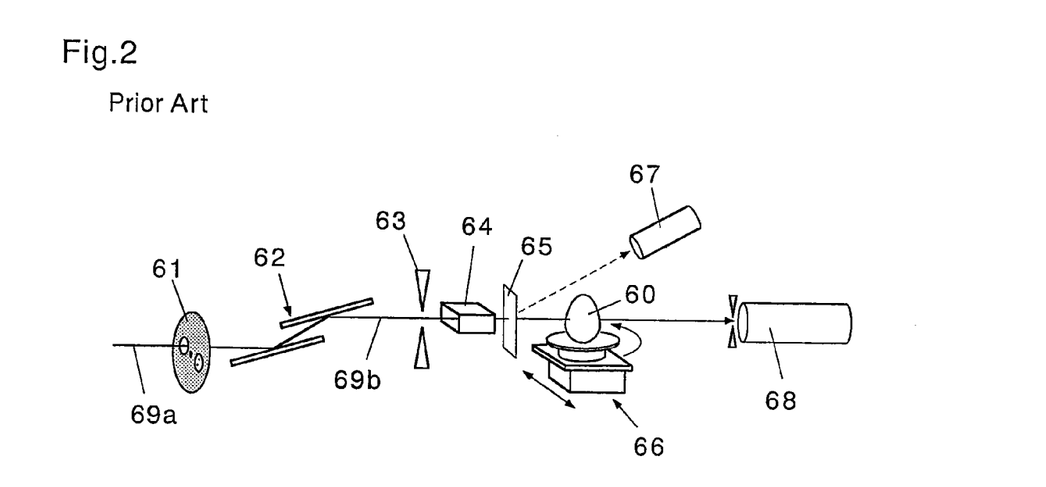
FIG. 2 is a schematic diagram of "Mixed Two-Color X-Ray CT Device" of Non-Patent Document 2.

As shown in FIG. 2, "Mixed Two-Color X-Ray CT Apparatus" of Non-Patent Document 2 includes a rotary filter 61, a monochromatic meter 62, a collimator 63, a transmission type ion chamber 64, a scattering member 65, a sliding rotary table 66, an NaI detector 67 and a plastic scintillation counter 68. A dominant wave X-ray of 40 keV and a double higher harmonic wave X-ray of 80 keV are extracted from synchrotron radiation light 69a by the monochromatic meter 62, a mixture ratio of the 40 keV X-ray and 80 keV X-ray is regulated by the rotary filter 61, scattered X-ray spectrum from the scattering member 65 is observed by the NaI detector 67 to measure the mixture ratio, a size of a mixed two-color X-ray 69b is adjusted by the collimator 63, and the ray is transmitted through the transmission type ion chamber 64 and a subject 60. An intensity of the ray is measured by the plastic scintillation counter 68.

According to this apparatus, the measurement precision of the electron density is improved. Moreover, the apparatus is successful in preparation of an image of the electron density and an effective atomic number.

Figure 3:
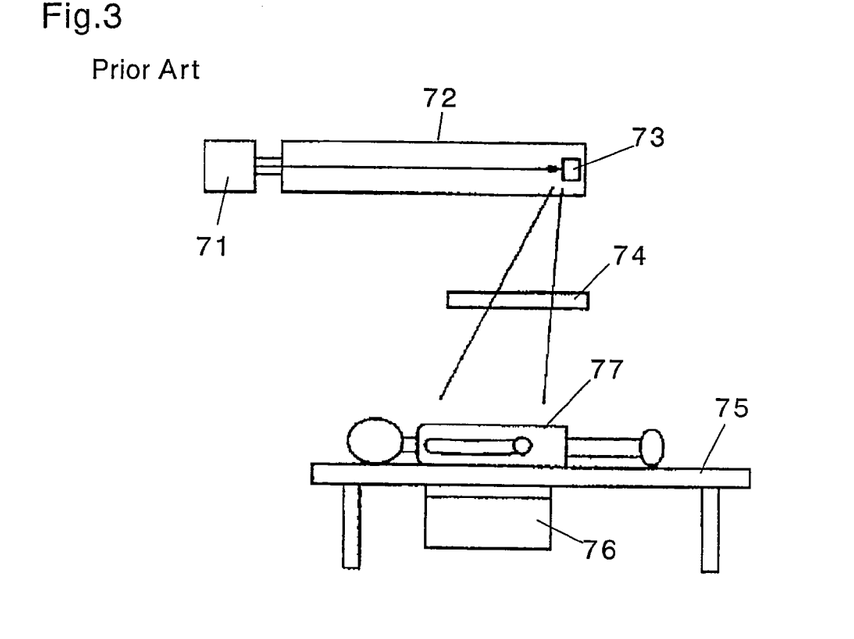
FIG. 3 is a schematic diagram of a diagnosis and curing apparatus of Patent Document 1.

As shown in FIG. 3, "X-Ray Diagnosis Apparatus and X-Ray Curing Apparatus" of Patent Document 1 is an X-ray diagnosis apparatus in which an X-ray blocking metal complex taken by a person 77 being inspected is selectively accumulated in an affected part of the person, and the part is irradiated with an X-ray from X-ray generation devices 71, 72 to form an X-ray image of the affected part with an X-ray image pickup device 76. A metal target 73 to generate a particular X-ray which belongs to a predetermined energy region is used, and an electron beam generated by the electron generator 71 and accelerated by the electron accelerator 72 is struck on the metal target 73 to generate the particular X-ray. The ray is used as the X-ray for irradiation.

It is to be noted that, in this drawing, reference numeral 74 is a filter device, and 75 is a bed.

Figure 4:
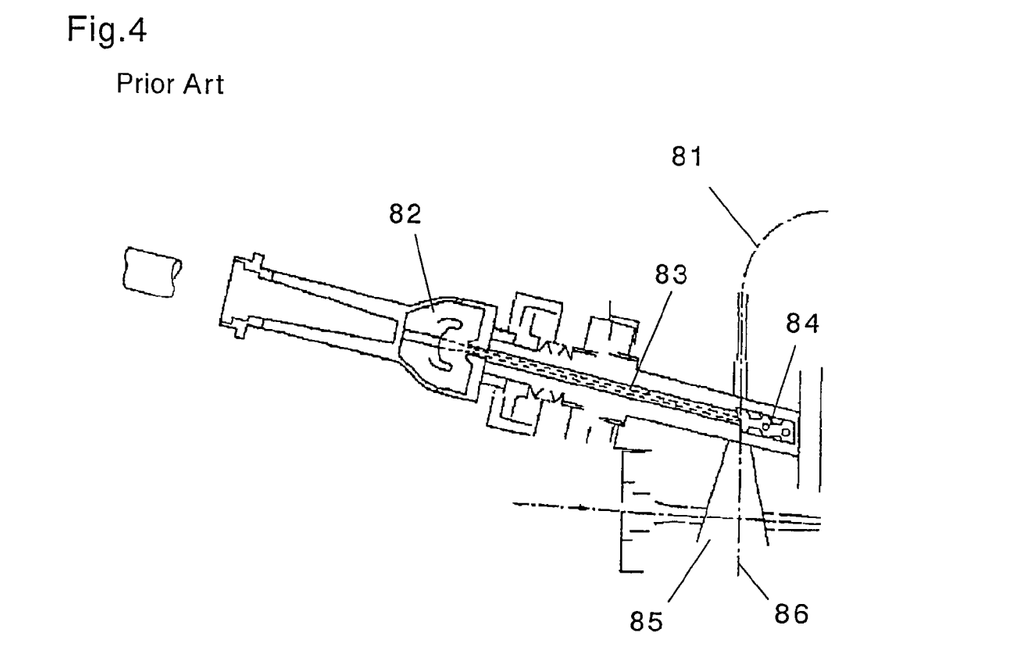
FIG. 4 is a schematic diagram of a diagnosis and curing apparatus of Patent Document 2.

Moreover, "Radiotherapy Apparatus having Low Dose Low Order and Portal Imaging X-Ray Source" of Patent Document 2 is an apparatus which is applicable to both of megavolt radiotherapy and diagnosis X-ray source for portal imaging. As shown in FIG. 4, both of an electron beam 81 (a high-energy curing source) emitted from an electron gun (not shown) and accelerated in a waveguide and an X-ray 85 (a low-energy diagnosis source) generated by collision of an electron beam 83 emitted from an electron gun 82 with a movable target 84 are arranged along the physically same line 86 of the apparatus. The apparatus also includes an actuator which moves the movable target 84 in an axial direction. The beams are arranged at positions for curing or diagnosis, if desired. The electron beam 81 is used for the curing, and the X-ray 85 is used for the diagnosis.

[Non-Patent Document 1]

"Development of Small-Sized Hard X-Ray Source using X-band Liniac", 2002, authored by Katsuhiro DOHASHI, et al.

[Non-Patent Document 2]

"Development of Mixed Two-Color X-Ray CT System" authored by Makoto SASAKI, et al., Medical Physics Vol. 23 Supplement No. 2 April 2003

[Patent Document 1]

Japanese Patent Application Laid-Open No. 2003-38475 titled "X-Ray Diagnosis Apparatus and X-Ray Curing Apparatus"

[Patent Document 2]

Japanese Patent Application Laid-Open No. 8-206103 titled "Radiotherapy Apparatus having Low Dose Low Order and Portal Imaging X-Ray Source"

Since the "monochromatic hard X-ray" having a narrow band and high energy is used in the X-ray for diagnosis, a clear image can be obtained. Moreover, a patient does not have to be uselessly irradiated with radiation.

Moreover, since a ray position of the X-ray for curing is disposed close to a light source of the X-ray for diagnosis, an error of an X-ray irradiation position can be reduced.

Therefore, to perform the diagnosis and the curing with the same apparatus, there has been a strong demand for an X-ray switching and generation device in which the monochromatic hard X-ray as the X-ray for diagnosis and the particular X-ray as the X-ray for curing are switched and generated at the same light source position.

In the diagnosis and curing apparatus of Patent Document 1, the particular X-ray which belongs to the predetermined energy region is used in both of the diagnosis and the curing. However, this particular X-ray has X-ray energy of 40 keV or more, and has a low absorption ratio with respect to a human body, but this ray is not monochromatic (i.e., has a broad band). Therefore, to obtain the clear image, a c-line blocking metal complex needs to be selectively accumulated of the affected part of the person being inspected. The ray has low energy and broad band even as the X-ray for curing. Therefore, the X-ray blocking metal complex needs to be accumulated in the affected part, and there has been a problem that a large burden is imposed on the person being inspected.

Moreover, in the diagnosis and curing apparatus of Patent Document 2, the electron beam is used for the curing, and the X-ray is used for the diagnosis. However, the X-ray is used for diagnosis, the X-ray for curing is required. Therefore, the apparatus becomes complicated and expensive.

To obtain the monochromatic hard X-ray from the radiation light, as disclosed in Non-Patent Document 2, the monochromatic meter including two crystal plates can be used. However, since the radiation light source is a large-sized facility, there is a problem that even for research or medical treatment the light cannot easily be introduced.

Moreover, in a case where two types of X-rays are used in order to improve the precision of the X-ray image during the X-ray diagnosis and measure both of the distributions of the electron density and the effective atomic number, a crystal angle of the monochromatic meter needs to be precisely regulated. Therefore, it is very difficult to switch the rays at a high speed in a short time.

Furthermore, in a case where the mixed two-color X-ray obtained by mixing the dominant wave X-ray and the double higher harmonic wave X-ray are mixed is extracted from the synchrotron radiation light as in Non-Patent Document 2, the wavelength of the X-ray is limited to that of the higher harmonic wave. There is also a problem that the dominant wave cannot be separated from the higher harmonic wave.

The present invention has been developed in order to satisfy the above demands. That is, an object of the present invention is to provide a device for switching/generating X-rays for diagnosis and curing in which a monochromatic hard X-ray as the X-ray for diagnosis and a particular X-ray as the X-ray for diagnosis can be switched and generated in order to perform the diagnosis and the curing with the same apparatus.

SUMMARY OF THE INVENTION

According to the present invention, there is provided a device for switching/generating X-rays for diagnosis and curing, comprising:

an electron beam generation device which accelerates a pulse electron beam to transmit the beam through a predetermined rectilinear orbit;

a laser generation device which generates a pulse laser light;

a laser light introduction device which introduces the pulse laser light onto the rectilinear orbit so as to collide with the pulse electron beam;

a metal target which generates a particular X-ray by collision with the pulse electron beam; and a target moving device which moves the metal target between a collision position on the rectilinear orbit and a retreat position out of the orbit, wherein at the collision position, a collision surface of the metal target is positioned spatially at the same position as a collision point between the pulse electron beam and the pulse laser light, the metal target is positioned at the retreat position, and the pulse electron beam collides head-on with the pulse laser light on the rectilinear orbit to generate a monochromatic hard X-ray for diagnosis, the metal target is positioned at the collision position, and the pulse electron beam collides with the metal target to generate the particular X-ray from the same collision point, and the X-rays for diagnosis and curing are emitted from the same light source position of the same apparatus.

According to a preferable embodiment of the present invention, the metal target is made of tungsten, iron, cobalt, nickel, copper, molybdenum, silver or an alloy of these metals.

Moreover, it is preferable to further comprise a collimator which is disposed between the collision point and a person being inspected and which controls radiating directions of the monochromatic hard X-ray for diagnosis and the particular X-ray for curing.

Furthermore, the laser generation device includes a plurality of pulse laser units which generate a plurality of pulse laser beams having different wavelengths;
a laser combining optical system which combines the plurality of pulse laser beams on the same optical path; and
a laser control unit which controls the plurality of pulse laser units so that the plurality of pulse laser beams have a time difference therebetween.

Moreover, it is preferable to further comprise a profile regulation optical system which regulates a beam profile of the pulse laser light at the collision point on the rectilinear orbit.

According to a constitution of the present invention described above, when the metal target is disposed at the retreat position, the pulse electron beam collides head-on with the pulse laser light on the predetermined rectilinear orbit to generate the "monochromatic hard X-ray".

When the metal target is disposed at the collision position, the "particular X-ray" is generated from the same light source position by the collision of the pulse electron beam and the metal target.

Therefore, when the target moving device simply moves the metal target to one of the "collision position" and the "retreat position", the monochromatic hard X-ray as the X-ray for diagnosis and the particular X-ray as the X-ray for curing can be switched and generated in the same apparatus. In consequence, both of X-ray sources for diagnosis and curing can be generated from the same collision point (the light source position) by use of the same electron beam, complete agreement of the light source position of the image for diagnosis with that of the X-ray for curing can be realized, and an error of an X-ray irradiation position can be eliminated in principle.

Moreover, in the present invention, since the pulse laser light collides head-on with the pulse electron beam on the rectilinear orbit to generate the monochromatic hard X-ray, collision efficiency can be maximized.

Furthermore, the wavelength of the X-ray generated by the collision of the pulse electron beam with the pulse laser light is determined depending on that of the laser light. Therefore, when the plurality of pulse laser beams having different wavelengths are generated by the laser generation device, two or more types of monochromatic hard X-rays can successively be switched and generated at a short time interval.

For example, when the laser beams having the plurality of types of wavelengths are alternately emitted and are allowed to collide with the electron beam during the collision of the electron beam with the laser light, two-color X-rays can alternately be generated. An electron density distribution and an element distribution can be obtained with high precision, and a sophisticated curing plan can be made.

Furthermore, the present invention is applicable to the curing combined with a drug delivery system by use of this hard X-ray.

DESCRIPTION OF THE PREFERRED EMBODIMENT

Preferable embodiments of the present invention will hereinafter be described with reference to the drawings. It is to be noted that, in the drawings, a common part is denoted with the same reference numeral, and redundant description is omitted.

Figure 5:
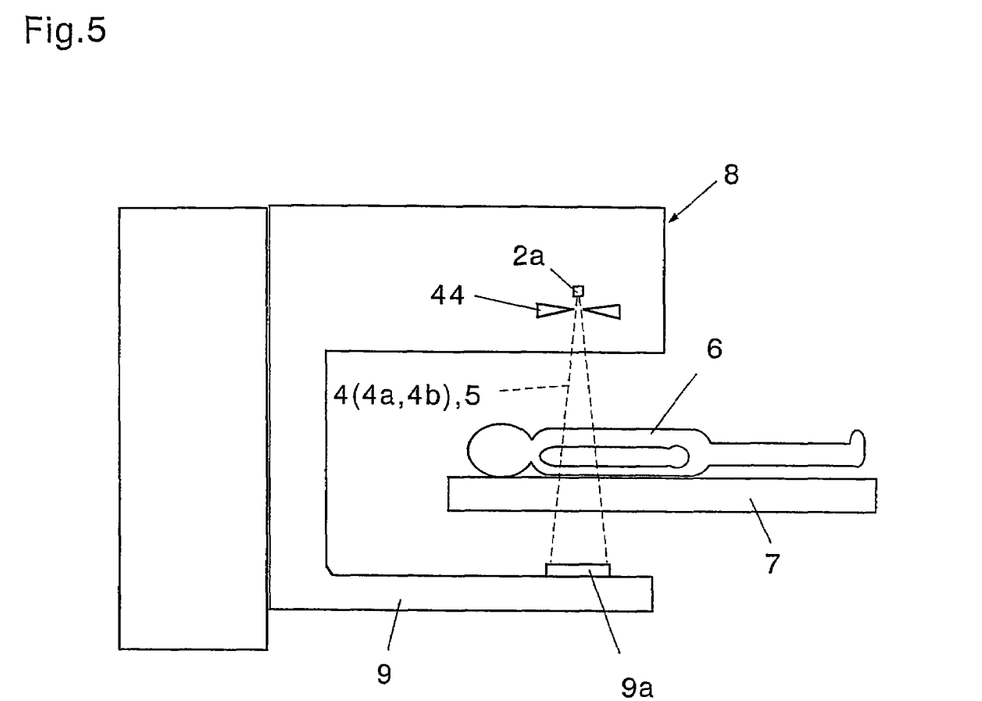
FIG. 5 is the whole constitution diagram of a diagnosis and curing apparatus in which a device for switching/generating X-rays for diagnosis and curing according to the present invention is used.

FIG. 5 is the whole constitution diagram of a diagnosis and curing apparatus including a device for switching/generating X-rays for diagnosis and curing according to the present invention. In the drawing, reference numeral 6 is a person being inspected, 7 is a movable bed on which the person being inspected is laid, 8 is a main body of the diagnosis and curing apparatus, and 9 is a movable arm including an X-ray detector 9a.

The device for switching/generating the X-rays for diagnosis and curing according to the present invention is incorporated in the main body 8. In the device, a monochromatic hard X-ray 4 as the X-ray for diagnosis and a particular X-ray 5 as the X-ray for curing are switched and generated to irradiate the person 6 being inspected.

The monochromatic hard X-ray 4 is a narrow-band X-ray of preferably about 10 to 40 keV, so that any X-ray blocking metal complex does not have to be accumulated in an affected part of the person and burdens to be imposed on the person can be reduced. The X-ray can be used in detecting absorption of the ray as a light source of X-ray CT by the X-ray detector 9a and reconstructing an image by a computer to obtain a two-dimensional sectional image of the person 6.

Moreover, it is preferable that the particular X-ray 5 is a high-energy X-ray of, for example, about 5 to 50 MeV which has little influence on a normal tissue in front of the affected part.

Figure 6:
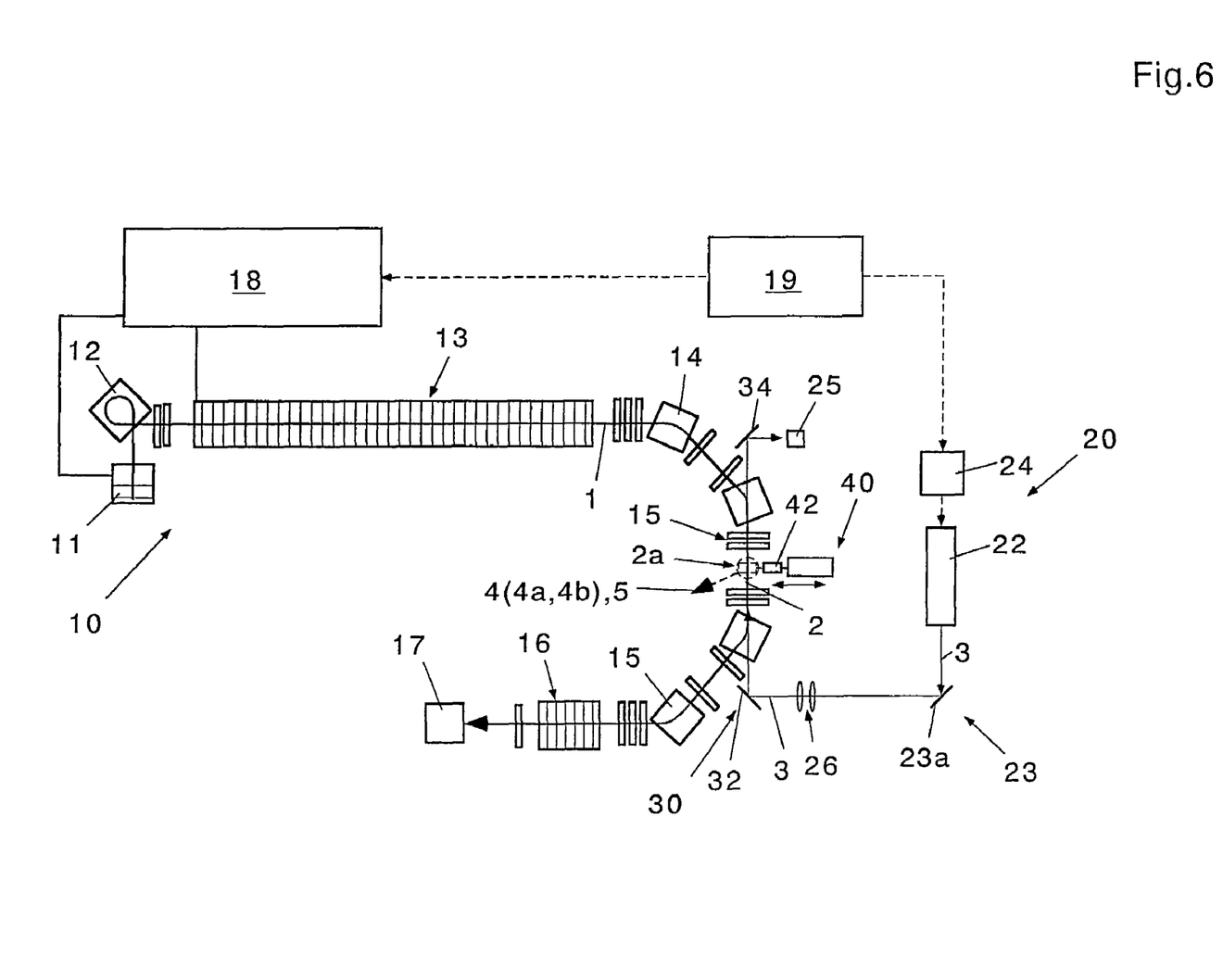
FIG. 6 is a diagram of a first embodiment of the device for switching/generating the X-rays for diagnosis and curing according to the present invention.

FIG. 6 is a plan view showing a first embodiment of the device for switching/generating the X-rays for diagnosis and curing according to the present invention. As shown in this drawing, a multicolor X-ray generation device of the present invention includes an electron beam generation device 10, a composite laser generation device 20, a laser light introduction device 30 and a target moving device 40.

The electron beam generation device 10 has a function of accelerating an electron beam to generate a pulse electron beam 1, and transmitting the beam through a predetermined rectilinear orbit 2.

In this example, the electron beam generation device 10 includes an RF electron gun 11, an α-magnet 12, an acceleration tube 13, a pending magnet 14, Q-magnets 15, a deceleration tube 16 and a beam dump 17.

The RF electron gun 11 and the acceleration tube 13 are driven by a high-frequency power source 18 of an X-band (11.424 GHz). An orbit of the electron beam drawn from the RF electron gun 11 is changed by the α-magnet 12. The beam then enters acceleration tube 13. The acceleration tube 13 is a small-sized X-band acceleration tube which accelerates the electron beam to generate a high-energy electron beam of preferably about 50 MeV. This electron beam is the multi-bunch pulse electron beam 1 of, for example, about 1 μs.

The pending magnet 14 bends the orbit of the pulse electron beam 1 with a magnetic field, transmits the beam through the predetermined rectilinear orbit 2, and guides the transmitted pulse electron beam 1 to the beam dump 17. A convergence degree of the pulse electron beam 1 is regulated by the Q-magnets 15. The pulse electron beam 1 is decelerated by the deceleration tube 16. The beam dump 17 traps the pulse electron beam 1 transmitted through the predetermined rectilinear orbit 2 to prevent leakage of radiation.

A synchronization device 19 executes control so that the electron beam generation device 10 is synchronized with the composite laser generation device 20, a timing of the pulse electron beam 1 is collided with that of the pulse laser light 3 described later and the pulse electron beam 1 collides with pulse laser light 3 at a collision point 2a (a light source position) on the predetermined rectilinear orbit 2.

By the electron beam generation device 10 described above, the multi-bunch pulse electron beam 1 of, for example, about 50 MeV, about 1 μs can be generated and transmitted through the predetermined rectilinear orbit 2.

The laser generation device 20 has a function of generating the pulse laser light 3. In this example, the laser generation device 20 has a pulse laser unit 22, a laser combining optical system 23, a laser control unit 24 and a laser dump 25.

The pulse laser unit 22 generates the pulse laser light 3 having a specific wavelength. For example, as the pulse laser unit 22, Nd-YAG laser having a wavelength of 1064 nm is used.

In this example, the laser combining optical system 23 includes a total reflection mirror 23a. The total reflection mirror 23a reflects the pulse laser light 3 of the pulse laser unit 22 toward a first mirror 32 of the laser light introduction device 30.

According to this constitution, the pulse laser light 3 can be reflected on the first mirror 32 and introduced onto the predetermined rectilinear orbit 2 of the pulse electron beam 1.

The laser control unit 24 controls the pulse laser unit 22. For example, when the pulse laser light 3 has a pulse oscillation number of 10 pps and a pulse width of 10 ns, the laser control unit performs the control so that the pulse electron beam 1 collides with the pulse laser light 3 at the collision position 2a of the predetermined rectilinear orbit 2 in response to a command from the synchronization device 19.

The laser dump 25 traps the pulse laser light 3 transmitted through the rectilinear orbit 2 and then returned to the laser generation device 20 via a second mirror 34 to prevent the light from scattering.

In FIG. 6, the X-ray generation device of the present invention further has a profile regulation optical system 26 between the first mirror 32 and the total reflection mirror 23a. This profile regulation optical system 26 is, for example, a composite lens, and regulates a beam profile (e.g., a size, a tilt and a position) of the pulse laser light 3 at the collision position 2a of the rectilinear orbit 2.

In this example, the laser light introduction device 30 has two mirrors 32, 34. A plurality of pulse laser beams 3 are introduced along the rectilinear orbit 2 so as to collide with the pulse electron beam 1 by the first mirror 32, and the pulse laser light 3 transmitted through the rectilinear orbit 2 is returned to the laser dump 25 of the laser generation device 20 by the second mirror 34. The first mirror 32 and the second mirror 34 may be total reflection mirrors.

According to the above-mentioned constitution, a wavelength of the X-ray generated by the collision of the pulse electron beam 1 with the pulse laser light 3 is determined depending on a wavelength of the pulse laser light 3. The monochromatic hard X-ray 4 can be generated by use of, for example, Nd-YAG laser having a wavelength of 1064 nm.

Moreover, the pulse laser light 3 collides head-on with the pulse electron beam 1 along the rectilinear orbit 2 to generate the monochromatic hard X-ray. Therefore, collision efficiency can be maximized.

It is to be noted that the pulse laser unit and the pulse laser light are not limited to this example, and ArF (wavelength of 193 nm), KrF (wavelength of 248 nm), XeCl (wavelength of 308 nm), XeF (wavelength of 351 nm) or Fe (wavelength of 157 nm) of excimer laser, a second higher harmonic wave (wavelength of 532 nm), a third higher harmonic wave (wavelength of 355 nm), a fourth higher harmonic wave (wavelength of 266 nm) or a fifth higher harmonic wave (wavelength of 213 nm) of YAG laser or the like may be used.

The target moving device 40 is an actuator which moves a metal target 42 between a collision position on the rectilinear orbit 2 and a retreat position out of the orbit. This actuator may be a translatory liquid pressure cylinder or a translatory electromotive cylinder.

It is to be noted that the target moving device 40 may be constituted so as to be manually operated in a case where a frequency of switching is small.

Efficiency of conversion of the pulse electron beam 1 which has collided with the metal target 42 is proportional to an atomic number of the target and an acceleration voltage of the electron beam. Therefore, to increase the conversion efficiency, as the target, a substance having a large atomic number, for example, tungsten, iron, cobalt, nickel, copper, molybdenum, silver or an alloy of these metals may be used.

Moreover, the collision position of the metal target 42 is set so that a collision surface of the metal target 42 is positioned spatially at the same position as that of the collision point 2a between the pulse electron beam 1 and the pulse laser light 3. This collision surface may be constituted so that the X-rays are generated in an irradiating direction of the X-rays (a downward direction in FIG. 5, a direction crossing a sheet surface of FIG. 6 at right angles).

According to the above constitution, the metal target 42 is positioned at the retreat position, and the pulse electron beam 1 is allowed to collide head-on with the pulse laser light 3 on the rectilinear orbit 2 to generate the monochromatic hard X-ray 4 from the collision point 2a.

Moreover, the metal target 42 is positioned at the collision position on the rectilinear orbit 2, and the particular X-ray 5 is generated from the same collision point 2a by the collision of the metal target 42 with the pulse electron beam 1.

Furthermore, when the acceleration voltage of the pulse electron beam 1 and a material of the metal target 42 are appropriately selected, the generated particular X-ray 5 can be regulated into the high-energy X-ray of about 5 to 50 MeV which has little influence on a normal tissue in front of the affected part of the person.

The monochromatic hard X-ray 4 and the particular X-ray 5 generated at the collision point 2a have little directivity, and are radiated from every direction. Therefore, as shown in FIG. 5, a collimator 44 may be disposed between the collision point 2a and the person 6 to control radiating directions of the monochromatic hard X-ray 4 and the particular X-ray 5.

Figure 7:
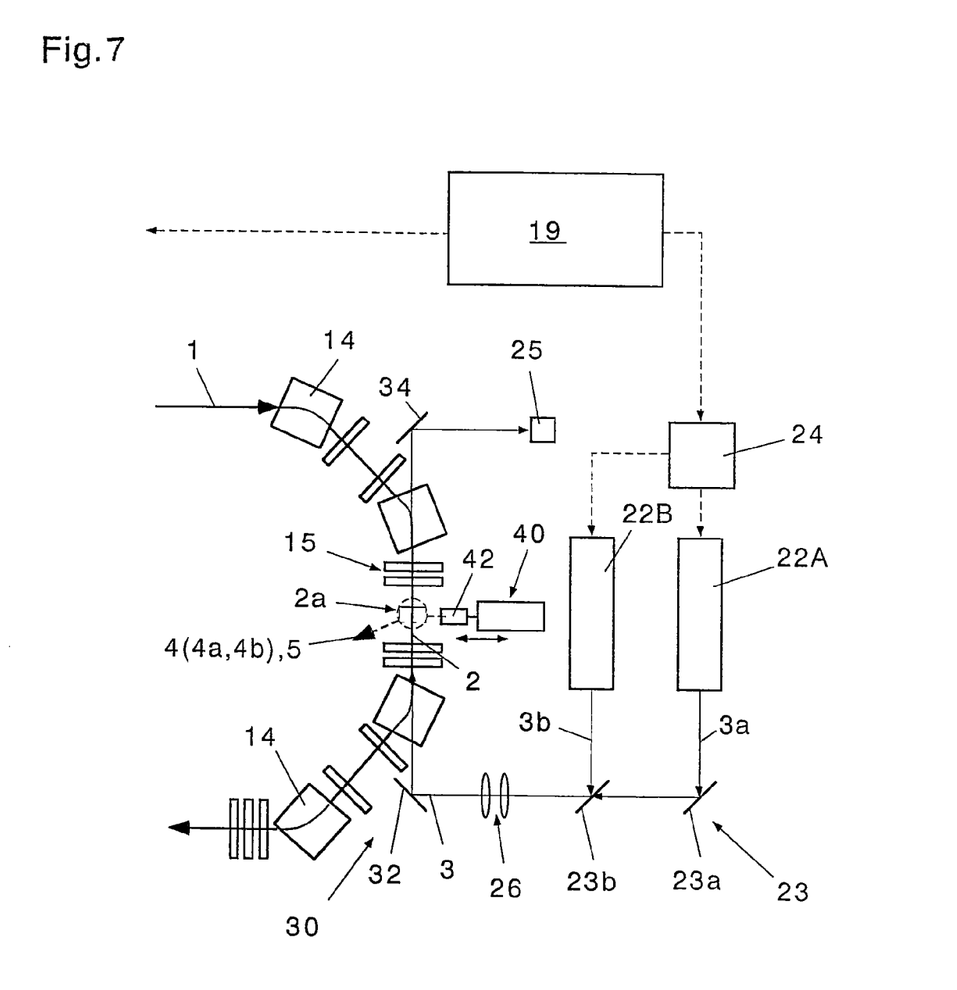
FIG. 7 is a diagram of a second embodiment of the device for switching/generating the X-rays for diagnosis and curing according to the present invention.

FIG. 7 is a diagram of a second embodiment of a device for switching/generating X-rays for diagnosis and curing according to the present invention. In this example, a laser generation device 20 has a plurality of pulse laser units 22A, 22B, a laser combining optical system 23, a laser control unit 24 and a laser dump 25.

The plurality of pulse laser units 22A, 22B generate a plurality of pulse laser beams 3a, 3b having different wavelengths. For example, as the pulse laser units 22A, 22B, Nd-YAG laser having a wavelength of 1064 nm and Nd-YAG laser obtained by incorporating KTP crystals in this Nd-YAG laser and having a wavelength of 532 nm are used. The wavelength is converted into a half wavelength by the crystals.

In this example, the laser combining optical system 23 includes a total reflection mirror 23a and a half mirror 23b. The total reflection mirror 23a reflects pulse laser light 3a of the pulse laser unit 22A toward a first mirror 32 of a laser light introduction device 30. The half mirror 23b is a half mirror through which the pulse laser light 3a can pass as it is, and the pulse laser light 3b is reflected toward the first mirror 32 of the laser light introduction device 30.

According to this constitution, the plurality of pulse laser beams 3a, 3b are combined on the same optical path, and are allowed to enter the first mirror 32 as pulse laser light 3. The plurality of combined pulse laser beams can be introduced onto a rectilinear orbit 2.

The laser control unit 24 controls the plurality of pulse laser units 22A, 22B so that the plurality of pulse laser beams 3a, 3b have a time difference therebetween. For example, each of the plurality of pulse laser beams 3a, 3b has a pulse oscillation number of 10 pps, and a pulse width of 10 ns. In this case, when one pulse oscillation time is shifted, the plurality of pulse laser beams 3a, 3b (wavelengths of 1064 nm and 532 nm) each having a pulse width of 10 ns are alternately output, and can be struck on the first mirror 32 as the pulse laser light 3.

Another constitution is similar to that of the first embodiment.

It is to be noted that the number of the pulse laser units is not limited to two, and three or more units may be used.

The pulse laser light is not limited to the above-mentioned examples, and ArF (wavelength of 193 nm), KrF (wavelength of 248 nm), XeCl (wavelength of 308 nm), XeF (wavelength of 351 nm) or F2 (wavelength of 157 nm) of excimer laser, a third higher harmonic wave (wavelength of 355 nm), a fourth higher harmonic wave (wavelength of 266 nm) or a fifth higher harmonic wave (wavelength of 213 nm) of YAG laser or the like may be used.

According to the constitution of the present embodiment, in the same manner as in the first embodiment, a metal target 42 can be positioned at a retreat position, and a pulse electron beam 1 can be allowed to collide head-on with the pulse laser light 3 on the rectilinear orbit 2 to generate a monochromatic hard X-ray. The metal target 42 may be positioned at a collision position on the rectilinear orbit 2 to allow the pulse electron beam 1 to collide with the metal target 42, and a particular X-ray 5 can be generated from the same collision point 2a.

Moreover, a wavelength of the X-ray generated by the collision of the pulse electron beam 1 with the pulse laser light 3 is determined depending on that of the pulse laser light 3. Therefore, when the plurality of pulse laser beams 3a, 3b having different wavelengths are generated by the composite laser generation device 20 according to this second embodiment, two or more types of monochromatic hard X-rays 4 (4a, 4b) can successively be switched and generated at a short time interval.

That is, the laser generation device can generate the pulse laser light in a short period (e.g., 10 pps or more). Therefore, when the laser control unit controls the plurality of pulse laser beams so as to make a time difference between the beams, the plurality of pulse laser beams are successively allowed to collide head-on with the pulse electron beam in a short period, and two or more types of plurality of monochromatic hard X-rays can successively be switched and generated in a short period (e.g., 10 pps or more).

Radiating directions of the monochromatic hard X-rays 4 (4a, 4b) and the particular X-ray 5 generated at the collision point 2a are controlled by the collimator 44, and the rays are radiated from the collision point 2a toward a person 6 as shown in FIG. 5.

The plurality of taken monochromatic hard X-rays 4 (4a, 4b) can be used in angiography and two-color X-ray CT, and the particular X-ray 5 can be used in curing the person 6.

Therefore, according to the second embodiment, the wavelengths of the X-rays can successively be switched at a high speed without physically moving the devices or components, a change of a subject with a wavelength switch time can be reduced, resolution of an X-ray image is improved, an electron density distribution and an element distribution can be obtained highly precisely, and a curing schedule can be sophisticated.

It is to be noted that the present invention is not limited to the above-mentioned embodiments. Needless to say, the present invention can variously be modified without departing from the scope of the present invention.

What is claimed is:

1. A device for switching/generating X-rays for diagnosis and curing, comprising:
   an electron beam generation device which accelerates a pulse electron beam to transmit the beam through a predetermined rectilinear orbit;
   a laser generation device which generates a pulse laser light;
   a laser light introduction device which introduces the pulse laser light onto the rectilinear orbit so as to collide with the pulse electron beam;
   a metal target which generates a particular X-ray by collision with the pulse electron beam; and
   a target moving device which moves the metal target between a collision position on the rectilinear orbit and a retreat position out of the orbit,
   wherein at the collision position, a collision surface of the metal target is positioned spatially at the same position as a collision point between the pulse electron beam and the pulse laser light,
   the metal target is positioned at the retreat position, and the pulse electron beam collides head-on with the pulse laser light on the rectilinear orbit to generate a monochromatic hard X-ray for diagnosis,
   the metal target is positioned at the collision position, and the pulse electron beam collides with the metal target to generate the particular X-ray from the same collision point, and
   the X-rays for diagnosis and curing are emitted from the same light source position of the same apparatus.

2. The device for switching/generating the X-rays for diagnosis and curing according to claim 1, wherein the metal target is made of tungsten, iron, cobalt, nickel, copper, molybdenum, silver or an alloy of these metals.

3. The device for switching/generating the X-rays for diagnosis and curing according to claim 1, further comprising:
   a collimator which is disposed between the collision point and a person being inspected and which controls radiating directions of the monochromatic hard X-ray for diagnosis and the particular X-ray for curing.

4. The device for switching/generating the X-rays for diagnosis and curing according to claim 1, wherein the laser generation device includes a plurality of pulse laser units which generate a plurality of pulse laser beams having different wavelengths;
- a laser combining optical system which combines the plurality of pulse laser beams on the same optical path; and
- a laser control unit which controls the plurality of pulse laser units so that the plurality of pulse laser beams have a time difference therebetween.

5. The device for switching/generating the X-rays for diagnosis and curing according to claim 4, further comprising:
- a profile regulation optical system which regulates a beam profile of the pulse laser light at the collision point on the rectilinear orbit.

* * * * *